United States Patent
Jackson

(10) Patent No.: US 6,673,017 B1
(45) Date of Patent: Jan. 6, 2004

(54) TEMPORAL RESOLUTION METHOD AND SYSTEMS FOR ULTRASOUND IMAGING

(75) Inventor: John I. Jackson, Menlo Park, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 10/230,488

(22) Filed: Aug. 28, 2002

(51) Int. Cl.⁷ .................................................. A61B 8/00
(52) U.S. Cl. ..................................................... 600/437
(58) Field of Search .............................. 600/437, 467, 600/438, 440, 441, 442, 443, 444, 447, 449, 450, 453, 455; 367/7, 11, 130, 138; 73/625, 626; 128/916

(56) References Cited

U.S. PATENT DOCUMENTS

| | | |
|---|---|---|
| 5,099,847 A | 3/1992 | Powers et al. |
| 5,976,088 A | 11/1999 | Urbano et al. |
| 5,980,458 A * | 11/1999 | Clark .......................... 600/437 |
| 6,139,500 A | 10/2000 | Clark |
| 6,353,752 B1 * | 3/2002 | Madore et al. ............. 600/410 |

* cited by examiner

Primary Examiner—Ali M. Imam

(57) ABSTRACT

Two or more temporal indicators are used for interleaving frames from a plurality of physiological cycles. For example, frames of one cycle are separated from the frames of another cycle based on an ECG signal. Data representing an imaged region for each of the frames is then used for temporally aligning the frames. For example, average velocity waveforms calculated from the frames of each of the cycles are fitted together. The temporal position of each of the frames within a base physiological cycle is determined based on the fitting. The interleaved frames provide a higher effective frame rate with improved temporal resolution which is based on the accurate interleaving of the data from the plurality of physiological cycles. Course alignment is provided using one event or temporal indicator. A more refined temporal alignment is provided in response to a second temporal indicator.

27 Claims, 3 Drawing Sheets

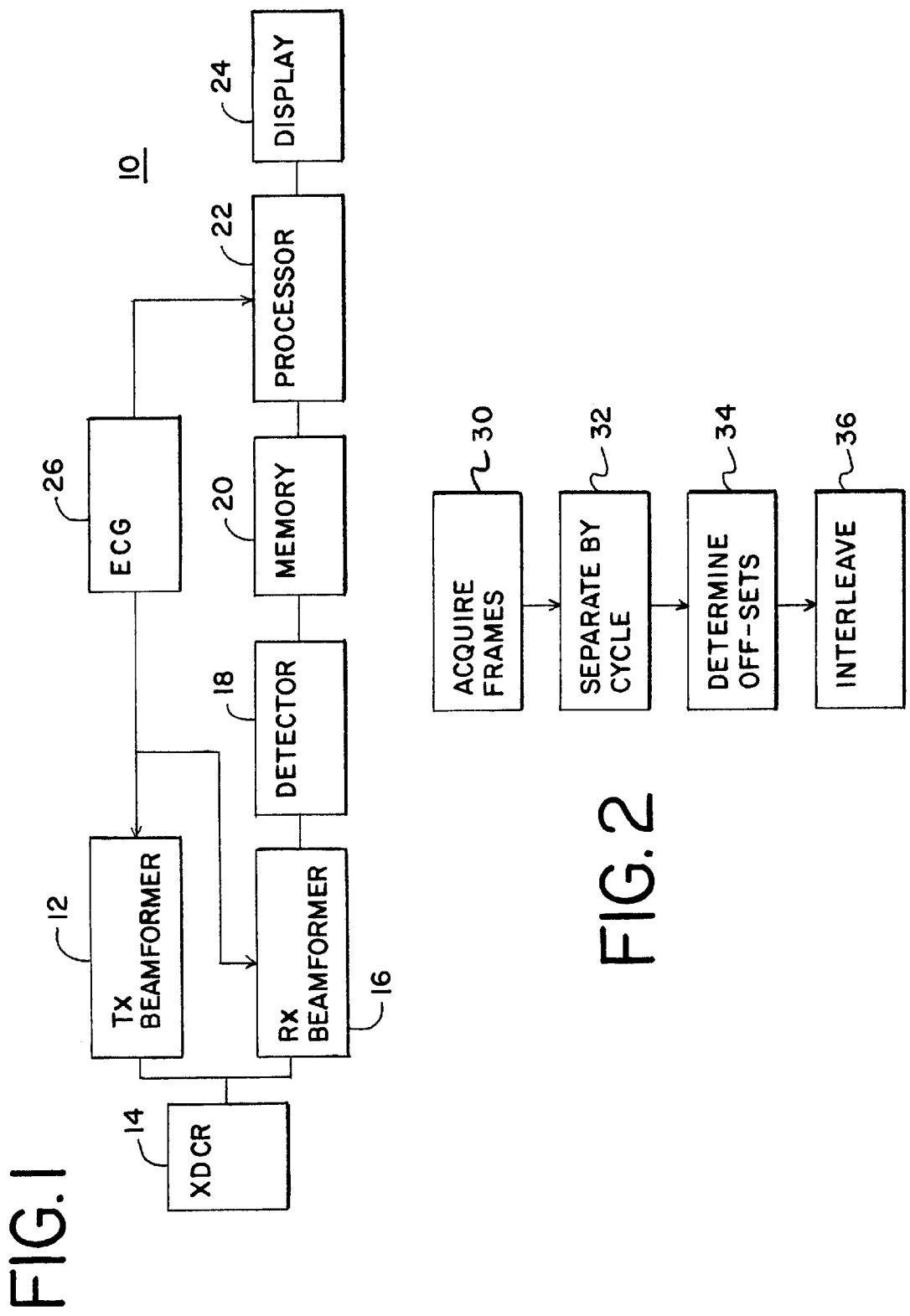

TEMPORAL RESOLUTION METHOD AND SYSTEMS FOR ULTRASOUND IMAGING

BACKGROUND

The present invention relates to ultrasound imaging of regions associated with cyclic motion. In particular, improved temporal resolution is provided by interleaving ultrasound images from two or more physiological cycles.

The effective frame rate is increased by interleaving frames or images from a plurality of cycles into a single cycle. U.S. Pat. No. 5,099,847 discloses triggering acquisition of frames at different times within different cycles. Once the frames are interleaved, the staggering delays used to trigger in the different cycles provide for an increased effective frame rate. U.S. Pat. No. 5,976,088 discloses increasing the effective frame rate by interleaving frames and filtering across physiologic cycles. For example, the first frames acquired in each of a plurality of cycles are filtered together. The second frames across the same physiological cycles are also filtered together. The process repeats for further frames.

Cardiac motion is adequately cyclic to interleave frames acquired with a frame rate of 15–20 hertz, such as associated with a 50–67 millisecond delay from one frame to the next. Interleaving frames from two cycles may double the frame rate where the frames represent different temporal positions within a cycle in each of the different cycles combined. To avoid overlapping representation of the same temporal location within a physiological cycle, the frames of data for the subsequent or second cycle are delayed by 25–33 milliseconds relative to frames of the first cycle. An R-wave or other trigger event is used to control acquisition timing throughout each cycle. However, delays from the trigger events may result in inaccuracies when high temporal resolution is desired. Cardiac events do not uniformly change so are not easily predictable. 10–20 millisecond variation in the total length of a cardiac cycle may be provided in a healthy individual. The length of successive cardiac cycles can easily vary by 5 to 10%, with variations up to 15% not being uncommon. For example, frame rates on the order of 100–300 Hertz (3–10 milliseconds per frame) are desired for myocardial imaging. Analysis of the deformation rate, also known as strain rate, of the heart requires temporal resolution on the order of 3 to 10 milliseconds. Using a delay from a trigger event may not be sufficiently accurate for interleaving the frames with high temporal resolution. Variations in the cycle and the equipment for detecting the cycle result in a resolution tolerance greater than 3–10 milliseconds per frame.

BRIEF SUMMARY

The present invention is defined by the following claims, and nothing in this section should be taken as a limitation on those claims. By way of introduction, the preferred embodiments described below include methods and systems for improving temporal resolution. Two or more temporal indicators are used for interleaving frames from a plurality of physiological cycles. For example, frames of one cycle are separated from the frames of another cycle based on an electrocardiogram (ECG) signal. Data representing an imaged region for each of the frames is then used for temporally aligning the frames. For example, average velocity waveforms calculated from the frames of each of the cycles are fitted together. The temporal position of each of the frames within a base physiological cycle is determined based on the fitting. The interleaved frames provide data representing the actual physiological cycle with a higher effective frame rate with improved temporal resolution. Course alignment is provided using one event or temporal indicator. A more refined temporal alignment is provided in response to a second temporal indicator.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of an ultrasound system for improving temporal resolution.

FIG. 2 is a flowchart diagram of one embodiment of a method for improving temporal resolution.

DETAILED DESCRIPTION OF THE PREFERRED EMBODIMENTS

Figure 3:
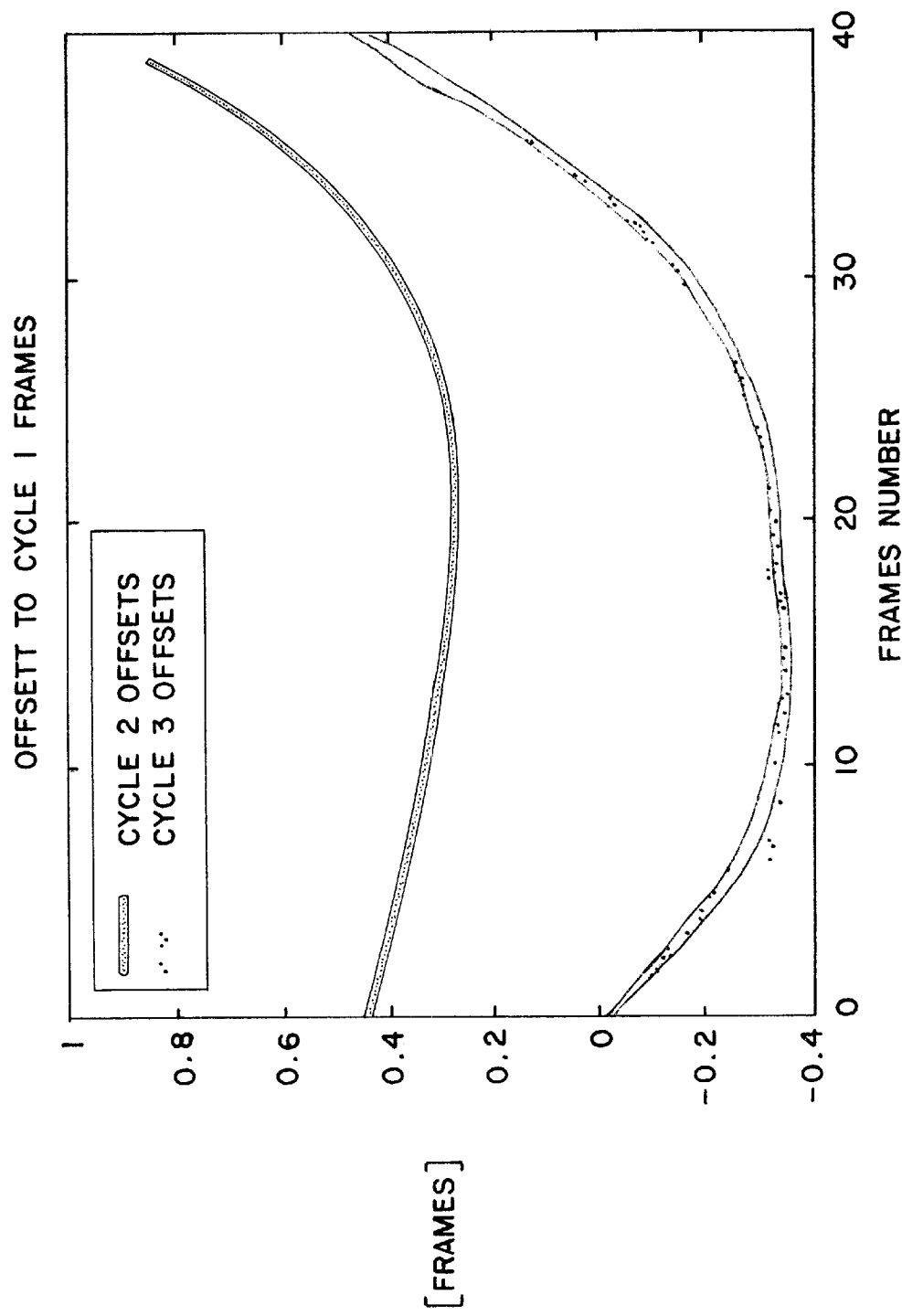
FIG. 3 is a graphical representation of one embodiment of temporal offsets associated with frames for different physiological cycles.

Frames from consecutive or nearly consecutive cycles are interleaved to achieve a higher effective frame rate. The interleaving is responsive to more than a single event or temporal indicator. For example, the temporal positioning of frames from different cycles relative to each other is responsive to both of an R-wave event and an analysis of ultrasound data. Any combination of two or more temporal indicators, such as an ECG and detection or tracking of tissue or fluid during the cycle, may be used. The signal-to-noise ratio may be further improved by filtering data from multiple cardiac cycles, such as filtering frames associated with a substantially same time within the cardiac cycle. By using frames from two or more cycles, temporal resolution is significantly improved.

FIG. 1 shows an ultrasound system 10 for improving temporal resolution. The system 10 includes a transmit beamformer 12, a transducer 14, a receive beamformer 16, a detector 18, a memory 20, a processor 22, a display 24 and an ECG monitor 26. Additional, different or fewer components may be provided, such as providing the memory 20, processor 22 and display 24 as part of a work station without the detector 18, receive beamformer 16, transducer 14 and transmit beamformer 12. In one embodiment, the system 10 comprises a Siemens Medical Solutions Elegra or Antares or an Acuson Sequoia®, Aspen™, Cypress® or 128 XP ultrasound system. Ultrasound systems by other manufacturers may be used.

The ECG monitor 26 comprises an electrode and processor for detecting cardiac cycle information, such as the R-wave or other cardiac cycle events. In alternative embodiments, a breathing cycle or other physiological cycle monitor is used. In yet other alternative embodiments, the ECG monitor 26 is optional. The ECG monitor 26 connects with the ultrasound system 10, such as connecting to an input to the processor 22, receive beamformer 16 and transmit beamformer 12. The ECG monitor 26 triggers operation of the transmit beamformer 12 and associated operation of the receive beamformer 16 and/or indicates a temporal position within a physiological cycle of frames generated by the transmit beamformer 12 and receive beamformer 16 with or without triggering. Either the trigger information, the amount of time since the last trigger, or identification of a particular temporal location within a heart cycle provided by the ECG monitor 26 is a temporal indication of the location within a cycle of each frame.

In response to a trigger signal or in response to other initiation, the transmit beamformer 12 generates a plurality of transmit waveforms. The transmit waveforms are provided to the transducer 14. In response, the transducer 14 generates acoustic energy focused along one or more scan lines. Reflected acoustic energy is received by the transducer 14. Electrical signals responsive to the acoustic echoes are provided to the receive beamformer 16. The receive beamformer 16 applies delays and appodization to generate data representing scan lines within an imaged region, such as a region associated with a heart or myocardium. The detector 18 detects information from the data. For example, the detector 18 detects an intensity of the echo signals, a velocity, variance or energy of moving tissue or fluid in the scanned region, or other characteristics as known or later developed for ultrasound imaging. By adjusting the focus of the transmit beamformer 12 and receive beamformer 16, the detector 18 outputs frames of data. Each frame of data represents one scan through the insonified region. By repeating the scan, a plurality of frames of data are generated. For example, frames representing the scanned region over two or more physiological cycles are acquired.

The memory 20 comprises a CINE memory, such as a random access memory. Other now known or later developed memories may be used, such as a VCR tape, DVD disk or hard drive. The memory 20 stores the plurality of frames representing the scanned region. Frames associated with two or more physiological cycles, such as subsequent physiological cycles, are stored for a later temporal alignment and associated interleaving.

The processor 22 comprises a general processor, an application specific integrated circuit, a digital signal processor, a system control processor, analog devices, digital circuits, or combinations thereof. As shown, the processor 22 is within a data pipeline between the memory 20 and the display 24. In alternative embodiments, the processor 22 is located elsewhere in the system 10 and data is transferred to or from the processor. Alternatively, the processor 22 may be located in a physically different location than the other components of the ultrasound system.

The processor 22 temporally interleaves frames from different physiological cycles into fewer cycles. The interleaving is performed as a function of at least two indications of time or events. Indications of relative time of frames are provided as an amount of delay after an R-wave or other event, a position of tissue, the velocity of tissue or blood, strain rate, or other information indicating a time within a physiological cycle.

Since data from different physiological cycles is interleaved into one physiological cycle, a base timeframe of reference is used. The base physiological cycle is an arbitrary cycle (e.g. an ideal cardiac cycle), one of the cycles during which frames are acquired (e.g. the first or subsequent cycles) or another physiological cycle.

Where an ECG monitor 26 is provided for cardiac imaging, an input to the processor 22 receives the ECG signal throughout the cardiac cycle or receives a trigger signal indicating a cardiac cycle event, such as an R-wave. The processor 22 distinguishes between different cycles for determining groupings of frames. In response to this indication of time within the physiological cycle, the frames from the memory 20 are separated as a function of the physiological cycle. In alternative embodiments, different trigger events, types of physiological cycles or types of time indicators are used for identifying frames of one cycle from frames of another cycle. The temporal location of the frames within the separated cycles is provided by this separation and the amount of delay from the beginning, end or other temporal location within each separate cycle.

Another indication of time or temporal location of frames within the base physiological cycle is determined by the processor 22. Data from the frames representing the scanned region is used to calculate a temporal location for any given frame. The processor interleaves the plurality of frames from different cycles as a function of the data representing the region in each of the frames. The data of any given frame represents the scanned region during a particular time within the physiological cycle. The scanned region changes as a function of time within each physiological cycle, so the characteristics of the data also change as a function of the temporal position within the physiological cycle.

The display 24 comprises a monitor, LCD, plasma screen, CRT or other now known or later device for displaying ultrasound images. The display 24 connects with the processor 22 through a scan converter or other image processing devices. In alternative embodiments, the processor and/or memory 20 operates on scan converted data. The frames of data from the plurality of physiological cycles are displayed as a single physiological cycle or as fewer cycles on the display 24. The interleaved frames of data have a frame rate greater than the frame rates of the frames acquired for each separate physiological cycle. For example, the frame rate of the interleaved frames is the sum of the acquisition frame rates of the separate physiological cycles. The frame rate of the interleaved frames may be less than the sum where frames from different physiological cycles are associated with a same time within the base physiological cycle or only a subset of frames are used for interleaving.

FIG. 2 shows a flow chart of one embodiment of a method for improving temporal resolution in ultrasound imaging. Two temporal indicators are used to identify the time associated with any given frame within a base cardiac or other physiological cycle. For example, R-wave triggers are used for initial registration of frames from at least two pluralities or groups of frames of the respective two physiological cycles. A second temporal indicator is provided by the data of the frames, such as tissue Doppler velocity data, B-mode data or strain rate data. Frames from a plurality of cycles are interleaved into the base cycle as a function of the identified temporal location of the frames. The resulting interleaved cycle has a frame rate greater than the acquisition frame rate of any of the component groups of frames from a single physiological cycle.

As shown in FIG. 2, frames associated with a plurality of cycles are acquired in act 30. The frames are separated into groups of frames associated with different cycles in act 32. A temporal offset relative to a base physiological cycle is determined for each frame within each group of frames in act 34. One temporal indicator may be used for the separation of act 32 and a different temporal indicator may be used for the offset determination of act 34. In alternative embodiments, both temporal indicators are used for one or both of acts 32 and 34. In act 36, the frames from a plurality of cycles are interleaved to form a cycle with a greater temporal resolution. The interleaving is a function of the temporal indicators based on the determined offsets. In alternative embodiments, other processes using two or more temporal indications of the relative position of one frame from one cycle to another frame from a different cycle may be used.

In act 30, a plurality of frames is acquired for each of at least two physiological cycles. Each of the frames represents a scanned region, such as a heart or vessel. The frames for each of the different physiological cycles are from subsequent or consecutive physiological cycles or from non-consecutive physiological cycles. The frames of each physiological cycle are acquired at a frame rate. The frame rate may be the same or different for each of the physiological cycles. For example, frames from two consecutive cardiac cycles are acquired at 50 or more frames per second. The frame rate of more than 50 frames per second, such as 75 frames per second, may allow viewing of the myocardium, but may not provide sufficient temporal resolution for a desired calculation of the strain rate.

In act 32, the frames of one physiological cycle are separated from the frames of other physiological cycles. In one embodiment, a cycle signal, such as an ECG signal, is monitored for a trigger event. For cardiac imaging, the trigger event comprises an R-wave or other event within the cardiac electrical cycle. In alternative embodiments, a cardiac event, such as the closure of the mitral valve, motion associated with the onset of isovolumic contraction or other visible or detectible cardiac event is used as the trigger event. The trigger event is a temporal indication of the beginning of one cycle or the end of another cycle. Based on the temporal indication, the frames of a first plurality of frames are separated from the frames of a second plurality of frames, resulting in groups of frames for each of two or more physiological cycles.

The trigger event identifies the separation of frames of one cycle from the frames of another cycle as well as the temporal position of each frame within each cycle. Within each cycle, each of the frames occurs at a known amount of time after the reoccurring trigger event. The frame rate may be constant, or may vary within or between cardiac cycles. In either case, the time when each frame of data is acquired, measured relative to the reoccurring trigger event, is known. In other alternative embodiments, a trigger event is used for only one of separating frames between cycles and determining a temporal position of a given frame within each cycle.

In act 34, temporal offsets of one frame of a cycle with respect to temporal positions of the base physiological cycle are determined. The temporal offsets are determined with any of the various indicators of time discussed above. In one embodiment, a plurality of frames corresponding to a first or other cycle are set as the base physiological cycle. For example, about 40 frames are acquired during the first cardiac cycle. The temporal position of frames from other cycles is then determined as an offset from a corresponding or nearest frame from the base physiological cycle or first cycle. FIG. 3 shows a graph of the offsets determined for frames associated with second and third cycles relative to a first cycle. The embodiment of FIG. 3 assumes that each plurality of frames associated with each cycle includes a same number of frames. The first frame of the subsequent cycle is determined to have an approximately 0.4 frame offset. For interleaving, the first frame of the second cycle would be positioned at a temporal location 0.4 frames (e.g. 0.4 the amount of time between the first and second frames of the base cycle) after the first frame of the base physiological cycle. As another example, the fifteenth frame of the third cycle has an offset determined to be about −0.35, so is positioned at a temporal location 0.35 frames prior to the fifteenth frame of the base physiological cycle. Each frame of the base physiological cycle is positioned throughout the cycle based on a frame rate or number of frames acquired throughout the cycle. Where a greater or lesser number of frames are acquired in a cycle as compared to the base physiological cycle, the offsets are determined from a closest temporal location of a frame of the base physiological cycle. In alternative embodiments, the off-sets are determined relative to a beginning or end of the cycle, as a position along a time axis with reference to another frame or using other processes.

In one embodiment, the offsets are determined as a function of data representing the region. As a result, the frames of data from different cycles are interleaved as a function of the data of the frames where the function of the data comprises an indication of the time associated with that frame within the base physiological cycle. Other temporal indicators may be used for determining the offset, such as an ECG trigger event, ECG signal, or user input indication of time.

In the embodiment using velocity of tissue data as an indicator of the time within the physiological cycle, a region of tissue is identified for one frame of data. For example, the user inputs a region of interest to identify a myocardial wall or other portion of the myocardium. Alternatively, the system 10 or processor 22 automatically identifies a desired tissue region using thresholding or other processes. The identified tissue or region of interest is then tracked through all or a subset of the frames of each cycle. For example, a user manually identifies the region of interest in each of the frames. As another example, the previously identified region of interest is tracked automatically by the system 10 using a 1 dimensional or 2-dimensional tracking algorithm. One tracking algorithm uses velocity information and the expected temporal difference or amount of time between frames to identify a search area in subsequent frames. Correlation or other processes are then used to search around the identified location for a best match of tissue or fluid structures. This automatic tracking continues for each subsequent frame to identify the region of interest in all or a subset of the frames.

Waveforms are calculated as a function of the region of interest for each of the cycles. For example, a mean velocity or weighted velocity of tissue, fluid, or tissue and fluid within the identified region of interest is calculated for each of the frames in two or more physiological cycles. The velocity information is calculated from Doppler data, but correlation or speckled tracking may be used. For each of the physiological cycles, the mean velocity or other data characteristic is plotted as a function of time or frame number.

The waveforms are compared. The waveforms of each cycle are fitted to a waveform of the base physiological cycle. For example, the mean velocity waveforms of the second and third cardiac cycles are fitted to a mean velocity waveform of a first cardiac cycle. The waveforms of various cycles may be longer or shorter than the base physiological cycle. For example, the beginning and associated end times of a physiological cycle may be shifted due to a different trigger event or delay of acquisition of the first frame after a trigger event than for the base physiological cycle. Local distortions may also occur in comparison of the waveforms. For example, systole may be relatively consistent between multiple cycles, but diastole waveform characteristics may vary from one cycle to another.

An algorithm is applied to generate the best fit of the waveforms to the base physiological cycle waveform. A temporal position within the base cardiac cycle is determined for each of the frames of each of the cycles in response to the best fit adjustments. Shifts along the temporal axis are determined as the offsets associated with any particular frame.

Figure 4:
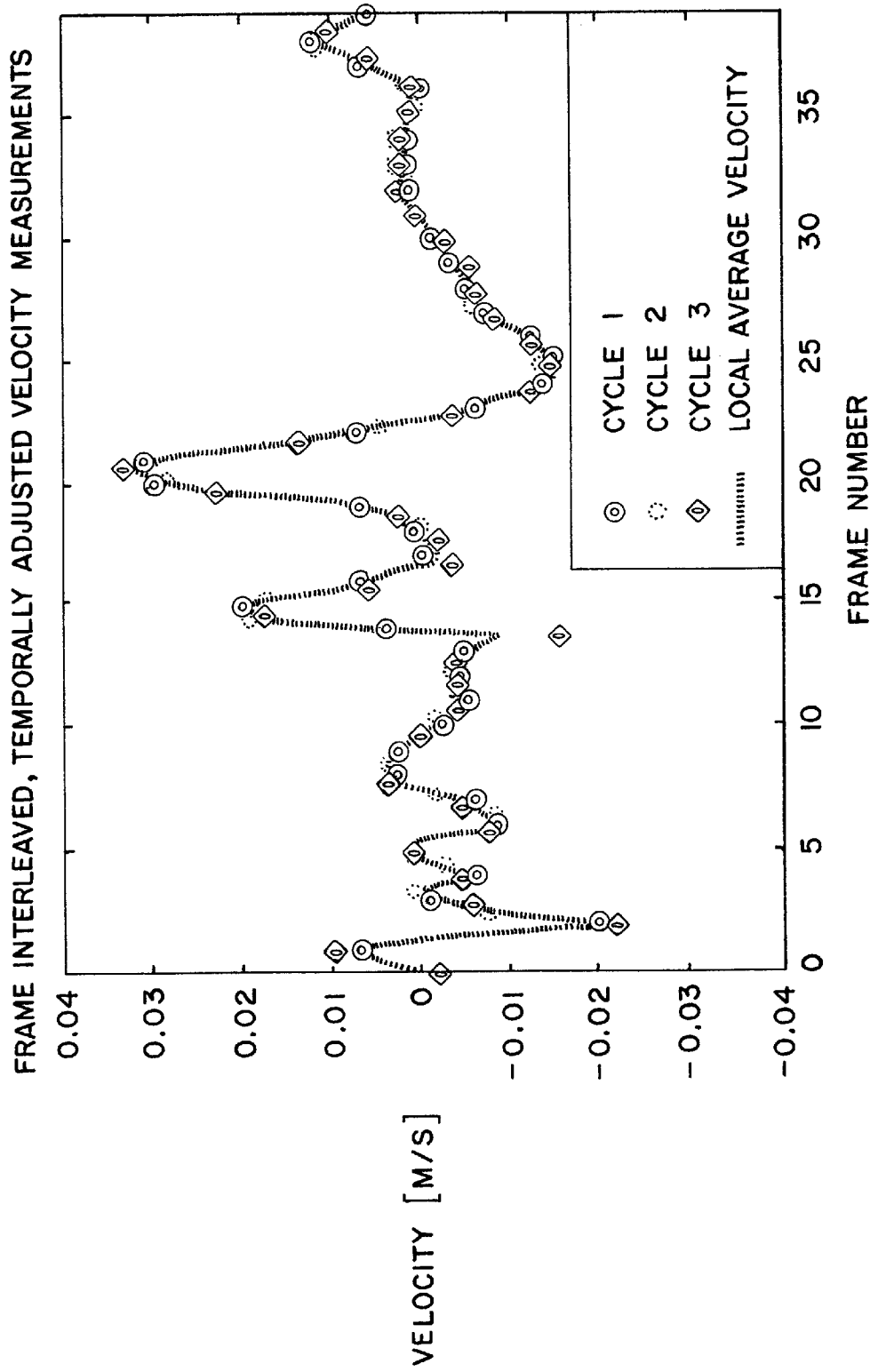
FIG. 4 is a graphical representation showing frame interleaved, temporally adjusted velocity measurements.

Any of various algorithms may be used for fitting the waveforms or otherwise determining temporal offsets for one group of frames relative to another group of frames. In one embodiment, an average velocity profile is calculated to determine local distortions or temporal shifts of one cycle relative to another cycle. First, the rough or estimated off-sets are determined. The offsets for the frames of each of the cycles are based on the mean velocity profile. For example, the mean velocity waveform from a first cycle is plotted. The mean velocity waveforms for subsequent cycles are scaled to have the same duration based on an offset from the beginning or end of the cycles. The mean velocity for each frame is plotted at the temporal location based on the scaled offset, such as using an amount of time from a trigger event to the acquisition of the frame. FIG. 4 shows a plot of mean velocity associated with each frame of three different cardiac cycles and resulting local average velocity. The frame number given in FIG. 4 is the frame number of the base physiological cycle, such as the first cycle. Where the second and third cycles have a same number of frames, the actual frame density along the frame number or temporal axis is three times the frame number or temporal density of the first cycle.

After temporally aligning the waveforms in response to one temporal indicator, the average velocity profile is calculated using a second temporal indicator such as the average of the mean velocity, for adjusting the temporal location associated with each frame. For example, the mean velocity within a region and frame i of cardiac cycle n is designated as $V_{ni}$. This mean velocity is convolved with a window function, such as a Gaussian, Hamming or other window function having an equivalent width of approximately one divided by the actual system frame rate (the time interval from one frame to a next frame in a given cycle). A series of Kronecker delta functions located at the same times as the mean velocity samples are convolved with the same window function discussed above. The curve resulting from the first convolution is divided by the curve resulting by the second convolution. The result of this division is a weighted velocity average across the cardiac cycle. The sum of the squared differences between individual velocity samples used in the first convolution and the weighted velocity average from the division is computed. The sum provides how far the actual temporal location of any given frame is from the actual average. The temporal offset associated with a given frame is then adjusted to minimize the error or difference from the average velocity profile.

To better account for local distortions, the cycle is divided into two or more temporal regions, such as four temporal regions. In one embodiment, the cycle is evenly divided, such as into groups of frames from a beginning to 24%, 25–49%, 50–74% and 75% to the end of the cycle. In other embodiments, the cycle is divided based on expected cycle variations, such as providing one temporal region associated with systole (e.g., a three hundred millisecond section of the waveforms) and two or more sections or temporal regions for the diastolic portion of the cardiac waveform. The error or adjustment to the averages is determined for each break point or division of the cycle. Offsets between the break points are linearly interpolated. In alternative embodiments, an adjustment of the temporal offset or error is calculated separately for each frame.

The average velocity profile analysis discussed above may be repeated, such as repeating the calculation of the weighted velocity average and the sum of the squared differences to minimize the sum of the squared differences. After one or more iterations, the adjustments in the offset determined from one temporal indicator (e.g. the velocity waveform) are applied to the offsets from the other temporal indicator (e.g. the time of each frame after the R-wave).

The adjusted offsets are used for interleaving the frames from various cycles into a single cycle in act 36. FIG. 4 shows the temporal positions of frames of data from three physiological cycles interleaved together as a single cycle based on at least two indications of the time position for each of the frames. In the embodiment shown in FIG. 4 and as described above, an ECG input determines an initial offset relative to frames of a first or base physiological cycle. A second temporal indicator, such as the mean velocity associated with a region of interest, is used to adjust the offsets for more accurate temporal location of frames from one cycle relative to frames of another cycle. The frames are then temporally aligned or interleaved based on the identified temporal position or offsets of each of the frames.

The interleaved frames provide greater temporal resolution. A greater effective frame rate is provided for the displayed interleaved frames than for frames from a non-interleaved cycle. For example, where the actual frame rate for acquisition of frames over a plurality of cycles is about 50 Hertz, the resulting effective frame rate by interleaving frames from two different cycles is about 100 Hertz. Displaying the interleaved frames at the greater effective frame rate provides a greater temporal resolution. At high frame rates, the user may be unable to discern the greater frame rates, but a greater amount of information is available to the user.

The additional information or increased temporal resolution may be used to improve calculations. For example, strain rate images are generated from the interleaved frames. The local gradient of velocity or other flow characteristic is calculated for each given time or frame. The width along the temporal dimension associated with each frame may vary as a function of the temporal position of the frame relative to adjacent frames. Improved temporal resolution results in improved strain rate information as a function of time for an identified scan line or region of interest.

Where two or more interleaved frames represent substantially a same time, such as frames within 3 milliseconds, 1 millisecond or other time period of an adjacent frame, the frames may be combined. For example, the frames are spatially filtered or averaged. A single frame is output from the filtering. In alternative or additional embodiments, the temporally aligned frames are spatially filtered throughout the cycle without reducing or minimal reduction in temporal resolution. In yet other alternative embodiments, areas within an interleaved cycle associated with no or a few numbers of frames are filled by interpolated or extrapolated information.

Various alternatives to using multiple temporal indicators or events for interleaving the frames from multiple cycles into a single frame may be used. In one embodiment, an R-wave or other trigger event is used to begin imaging of multiple cycles. In response to the R-wave or other trigger event, frames of different cycles are acquired in response to different offsets from the trigger. For example, frames for a complete cardiac cycle are acquired starting at the R-wave for one cycle, starting at the R-wave +5 milliseconds for another cycle, starting at the R-wave +10 milliseconds for yet another cycle and starting at the R-wave +15 milliseconds for a last cycle given a 50 Hertz actual frame rate. Since the cardiac cycle may vary from cycle to cycle, the R-wave based offsets of the frames within the cycle maybe inaccurate, especially later in the cycle. The drift from the desired temporal spacing is tracked using processes discussed above or in response to a second temporal indicator. The relative offset associated with any given frame from adjacent frames is then adjusted as a function of the tracked drift.

In another alternative embodiment, the weighted adjustment of temporal offsets is provided as a function of the position in the cardiac cycle. For example, the amount of time from a trigger event, such as an R-wave, is used to determine the temporal position of each frame within the cardiac cycle for interleaving. The acquisition of frames is not triggered from the trigger event, but instead the trigger event indicates a beginning or ending of the cycle. For frames associated with times later in the cardiac cycle, the amount of time from the trigger event is weighted less than an amount of time determined from a different temporal indicator. For example, a delay from a trigger event calculated based on data from the frames has an increased weight for later frames and a decreased weight for earlier frames. Different temporal indicators are used to determine a different temporal position for a same frame within a cycle. The different times for any given frame are then combined, such as averaged or weighted averaging.

Interleaving is used in one embodiment for three-dimensional imaging of a volume subject to cyclic motion. Spatially different sets of frames are acquired. During acquisition, a monitoring line, such as one or more scan lines in a same location within the volume, is repetitively (e.g., every 50 ms) acquired. The data from the monitoring line is used to track the cycle or as a temporal indicator for each of the frames regardless of spatial location.

In another embodiment, interleaved frames of data are used to generate M-mode-like images. For example, intensity, velocity, strain rate or other data from interleaved frames representing a same point, plurality of points, lines or region are displayed as a function of time (i.e. location along one axis, time along another axis and pixel modulation as a function of the data). Alternatively or additionally, strain or strain rate is calculated for one or more locations as a function of time. A graph of the strain, strain rate, average strain, average strain rate or other strain characteristic for each point, region or entire image area is generated as a function of time using the interleaved frames of data. Interleaving with high temporal resolution may provide more complete strain information.

While the invention has been described above by reference to various embodiments, it should be understood that many changes and modifications can be made without departing from the scope of the invention. For example, different temporal indicators may be used in a same or different way for determining a temporal location for interleaving relative to frames of other cycles. Both temporal indicators may be based on an amount of time from a same or different events within a cycle determined using the same or different information. As another example, one temporal indicator is used for a rough determination of the interleaved temporal location, such as a temporal indicator based on an ECG signal or triggered event or based on data within the frames. The other temporal indicator is used for adjusting the temporal location.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. A method for improving temporal resolution in ultrasound imaging, the method comprising:
    (a) acquiring a first plurality of frames representing a region during a first physiological cycle;
    (b) acquiring a second plurality of frames representing the region during a second physiological cycle, the second physiological cycle different than the first physiological cycle; and
    (c) temporally interleaving the first and second plurality of frames, the interleaving a function of at least two indications of a time relative to a base physiological cycle for each of the frames.

2. The method of claim 1 wherein (a) and (b) comprise acquiring the first and second pluralities of frames during cardiac cycles.

3. The method of claim 1 wherein (b) comprises acquiring the second plurality of frames during the second physiological cycle, the second physiological cycle a next physiological cycle after the first physiological cycle.

4. The method of claim 1 further comprising:
    (d) monitoring a cycle signal;
    wherein (c) comprises distinguishing between the first and second plurality of frames in response to the cycle signal, the cycle signal comprising one of the at least two indications of the time.

5. The method of claim 4 wherein (d) comprises monitoring an ECG signal.

6. The method of claim 4 wherein (c) further comprises interleaving as a function of an amount of time from a reoccurring trigger event of the cycle signal for each of the frames of the first and second pluralities.

7. The method of claim 1 wherein (c) comprises interleaving the first and second pluralities of frames as a function of data of the first and second pluralities of frames, the data representing the region, the function of the data comprising one of the at least two indications of time.

8. The method of claim 7 wherein (c) comprises interleaving the first and second pluralities of frames as a function of a position of tissue represented in each of the frames, the position of the tissue indicating the time in the base physiological cycle.

9. The method of claim 7 wherein (c) comprises interleaving the first and second pluralities of frames as a function of velocity data represented in each of the frames, the velocity data indicating the time in the base physiological cycle.

10. The method of claim 7 wherein (c) comprises interleaving the first and second pluralities of frames as a function of strain rate, the strain rate indicating the time in the base physiological cycle.

11. The method of claim 1 further comprising:
    (d) monitoring an ECG signal;
    wherein (c) comprises distinguishing between the first and second plurality of frames in response to the ECG signal, the ECG signal comprising a first one of the at least two indications of the time; and
    further comprising:
    (e) identifying a temporal position of each frame of the first and second pluralities of frames based on data representing the region of the frames, the temporal position comprising a second one of the at least two indications of time.

12. The method of claim 1 wherein (c) comprises identifying a time within the base physiological cycle based on an ECG input and data of the frames representing the region.

13. The method of claim 1 wherein (a) comprises acquiring the first plurality of frames at a first frame rate, and (b) comprises acquiring the second plurality of frames at a second frame rate the same or different than the first frame rate;

further comprising:
(d) displaying the interleaved first and second pluralities of frames at a third frame rate, the third frame rate greater than either of the first and second frame rates.

14. The method of claim 13 wherein the region comprises a myocardium, the physiological cycle comprises a heart cycle and (a) and (b) comprise acquiring at the first and second frame rates being at least 50 Hz and (d) comprises displaying at the third frame rate being at least 100 Hz.

15. The method of claim 1 further comprising:
(d) filtering at least two frames associated with a substantially same time of the base cardiac cycle.

16. The method of claim 1 further comprising:
(d) repeating (a), (b), and (c) for different spatial locations in a volume; and
(e) transmitting a monitoring line at a same location for each repetition of (d).

17. The method of claim 1 wherein (c) comprises interleaving the first and second pluralities of frames as a function of velocity data represented in each of the first and second pluralities of frames, the velocity data indicating the time in the base physiological cycle and representing the region, the function of the velocity data comprising a first one of the at least two indications of time.

further comprising:
(d) monitoring an ECG signal;
wherein (c) comprises distinguishing between the first and second plurality of frames in response to the ECG signal, the ECG signal comprising a second one of the at least two indications of the time.

18. The method of claim 1 further comprising:
(d) generating a graph of a strain characteristic as a function of time from the temporally interleaved first and second plurality of frames.

19. The method of claim 1 further comprising:
(d) generating a display of spatial locations as a function of time.

20. An ultrasound system for improving temporal resolution, the system comprising:
a memory for storing first and second pluralities of frames representing a region during first and second physiological cycles, the second physiological cycle different than the first physiological cycle; and
a processor for temporally interleaving the first and second plurality of frames, the temporal interleaving a function of at least two indications of a time relative to a base physiological cycle for each of the frames.

21. The system of claim 20 further comprising:
an ECG monitor input connected with the processor for monitoring a cardiac cycle signal;
wherein the processor is operable to distinguish between the first and second plurality of frames in response to the cardiac cycle signal, the cardiac cycle signal comprising one of the at least two indications of the time.

22. The system of claim 21 wherein the processor is operable to interleave the first and second pluralities of frames as a function of an amount of time from a trigger event of the ECG signal and as a function of an identified temporal position of each frame of the first and second pluralities of frames based on data representing the region of the frames, the temporal position comprising a second one of the at least two indications of time.

23. The system of claim 20 wherein the processor is operable to interleave the first and second pluralities of frames as a function of data of the first and second frames, the data representing the region, the function of the data comprising one of the at least two indications of time.

24. The system of claim 23 wherein the function of the data comprises at least one of: (i) a position of tissue represented in each of the frames, the position of the tissue indicating the time in the base physiological cycle, (ii) velocity data represented in each of the frames, the velocity data indicating the time in the base physiological cycle and (iii) strain rate, the strain rate indicating the time in the base physiological cycle.

25. The system of claim 20 wherein the first and second plurality of frames are associated with first and second frame rates, respectively, the second frame rate the same or different than the first frame rate; and further comprising a display connected with the processor, the display operable to display the interleaved first and second pluralities of frames at a third frame rate, the third frame rate greater than either of the first and second frame rates.

26. A method for improving temporal resolution in ultrasound imaging, the method comprising:
(a) acquiring first and second pluralities of frames representing a region during first and second cardiac cycles at first and second frame rates, respectively;
(b) identifying times within a base cardiac cycle for each of the frames of the first and second pluralities of frames based on an ECG signal and data of the frames of the first and second pluralities of frames, the data representing the region; and
(c) interleaving the frames of the first and second cardiac cycles into the base cardiac cycle as a function of the identified times, the base cardiac cycle having a third frame rate greater than either of the first and second frame rates.

27. The method of claim 26 wherein (b) comprises:
(b1) separating frames of the first plurality from frames of the second plurality based on the ECG signal;
(b2) calculating first and second waveforms as a function of the data of the frames for each of the first and second cardiac cycles;
(b3) temporally fitting the first and second waveforms to the base cardiac cycle, a temporal position within the base cardiac cycle for each of the frames of the first and second pluralities responsive to the fitting; and
(b4) interleaving the frames of the second plurality with the first plurality as a function of the temporal position of each frame of the first and second pluralities.

* * * * *